United States Patent
Chang et al.

(10) Patent No.: US 6,889,179 B2
(45) Date of Patent: May 3, 2005

(54) METHOD OF SIMULATING ENVIRONMENTAL EXPOSURE

(75) Inventors: Xiaoyuan Chang, Manlius, NY (US); Sandra Jayne Downey, Cazenovia, NY (US)

(73) Assignee: Carrier Corporation, Syracuse, NY (US)

( * ) Notice: Subject to any disclaimer, the term of this patent is extended or adjusted under 35 U.S.C. 154(b) by 665 days.

(21) Appl. No.: 09/947,724

(22) Filed: Sep. 6, 2001

(65) Prior Publication Data

US 2003/0046048 A1 Mar. 6, 2003

(51) Int. Cl.[7] ................................................ G06F 7/48
(52) U.S. Cl. ......................................................... 703/6
(58) Field of Search ............................... 703/6; 73/1.03, 73/335.06, 864.81; 422/109; 435/303.1; 436/183

(56) References Cited

U.S. PATENT DOCUMENTS

| | | | | |
|---|---|---|---|---|
| 4,269,057 A | * | 5/1981 | Ong et al. | 73/1.03 |
| 5,010,777 A | * | 4/1991 | Yehl et al. | 73/864.81 |
| 5,792,427 A | * | 8/1998 | Hugh et al. | 422/109 |
| 6,117,687 A | * | 9/2000 | Hugh | 436/183 |
| 6,503,751 B2 | * | 1/2003 | Hugh | 435/303.1 |

OTHER PUBLICATIONS

Haynes, Development of Accelerated Aging Test for ESD/EMI Protective Materials and Electrical Discontinuity at Seams and Interconnections, IEEE, Electrical Overstress/Electrostatic Discharge Symposium, Sep. 1999, pp. 282–286.*

Hernandez et al., A Study on the Effect of Environmental Stresses on the Hydrophobic Characteristics and Field Performance of RTV Silicone Coatings, IEEE, 1999 Annual Report Conference on Electrical Insulation and Dielectric Phenomena, vol. 2, Oct. 1999.*

Lessner et al., Quantitative Measurement of the Degradation of EMI Shielding and Mating Flange Materials After Environmental Exposure, 1993 IEEE Int. Symposium on Electromagnetic Compatibility, Aug. 1993, pp. 207–213.*

Shook et al., Influence of Preheat and Maximum Temperature of the Solder–Reflow Profile on Moisture Sensitive IC's, IEEE, 47th Electronic Components and Technology Conference, May 1997, pp. 1041–1048.*

Moore et al., Permittivity of Fiber Polymer Composites Environmental Effects: Comparison of Measurement and Theory, IEEE, Antennas and Propagation Society Int. Symposium, May 1990, pp. 1204–1207.

Gore et al., Corrosive Gas Environmental Testing for Electrical Contacts, IEEE Transactions on Components, Hybrids, and Manufacturing Technology, vol. 13, No. 1, Mar. 1990, pp. 27–32.

Williams, The Effect of Test Environment on the Creep of Base Metal Surface Films Over Precious Metal Inlays, IEEE Transactions on Components, Hybrids, and Manufacturing Technology, vol. 11, No. 1, Mar. 1988, pp. 36–42.

Baron et al., Search for Test Simulating the Environment of Industrial Atmospheres for Contacts and Connections, IEEE Transactions on Components, Hybrids, and Manufacturing Technology, vol. 2, No. 3, Sep. 1979, pp. 343–359.

* cited by examiner

Primary Examiner—Russell Frejd
(74) Attorney, Agent, or Firm—Carlson, Gaskey & Olds

(57) ABSTRACT

An environmental simulation test utilizes various temperatures and exposure times while exposing a test item to wet and dry conditions. In one example a marine environment where there is some pollution is simulated using a 24 hour test cycle that may be repeated as many days as necessary. The test cycle includes spraying a solution onto a test item and then cyclically exposing the test item to dry and humidified conditions.

15 Claims, 3 Drawing Sheets

METHOD OF SIMULATING ENVIRONMENTAL EXPOSURE

BACKGROUND OF THE INVENTION

In general terms, this invention relates to a method of simulating environmental exposure of an item over time.

A variety of commercial goods are exposed to environmental factors over time, which affect the lifetime or performance of the product. Air conditioning systems include various components that are exposed to environmental factors during the service life of the components. It is desirable to simulate the effects of the environmental factors on the various components over time to permit design improvements or adjustments to increase the quality or length of service of the various components.

A variety of environmental simulation tests are known. Most tests have been designed for particular items or industries. For example, the automotive industry has several known tests used to simulate environmental effects on vehicle bodies and engines. Additionally, tests vary depending on the expected environment in which the item of interest will be utilized.

Within the air conditioning industry, several tests have been used. One popular test is known as the prohesion cyclic corrosion test. During this test, an electrolyte spray is applied at a temperature of 25° C. for a period of about one hour. The item is then dried for about one hour at a temperature of 35° C. The spray and dry cycles are then repeated many times over. The solution sprayed upon the test item typically has a content including 0.05% NaCl and about 0.35% $(NH4)_2SO_4$ with a pH within the range from about 5.0 to about 5.4. While the prohesion test does provide some acceleration of the effects of environmental exposure, the acceleration is not fast enough to provide meaningful results to facilitate effectively evaluating new products.

Additionally, with known methods there is a difficulty in correlating the test results to actual environmental conditions.

Accordingly, there is a need for an improved environmental simulation process. This invention addresses that need while avoiding the shortcomings of prior methods.

SUMMARY OF THE INVENTION

In general terms, this invention is a method of simulating the effects of environmental exposure on an item. The inventive method includes utilizing different amounts of time and temperatures while exposing the item to wet and dry conditions, respectively.

In one example use of the inventive method, the item of interest is wetted with a solution when the item is at a first temperature for a first length of time. The item is then dried for a second length of time that is less than the first length of time at a second temperature that is higher than the first temperature. The item is then dried for a third length of time that is less than the second length at a third temperature that is lower than the second temperature but higher than the first temperature. The item is then exposed to humidity at a third temperature for the same amount of time that the item was wetted with the solution. The item is then dried for the second length of time at a fourth temperature that is higher than the second temperature. The steps of drying the item at the third temperature for the third length of time, humidifying the item at the third temperature for the first length of time and then drying the item for the second length of time at the fourth temperature preferably are then sequentially repeated twice. After that series of steps, the item is then dried again for the third length of time at the third temperature and humidified at the third temperature for the first length of time. After that, the item is dried again at the first temperature but for a fourth length of time that is between the second and third lengths of time.

In one example where the inventive method simulates a marine environment, the item is wetted with a solution at about 35° C. for about three hours. The item is then dried for about 1 hour and 45 minutes at about 55° C. The item is then dried for about 15 minutes at about 50° C. The item is then humidified at about 50° C. for about 3 hours. Next the item is dried for about 1 hour and 45 minutes at about 60° C. The steps of drying the item for about 15 minutes at about 50° C., humidifying the item at about 50° C. for about 3 hours and drying the item for about 1 hour and 45 minutes at about 60° C. are then repeated sequentially twice. After that, the item is again dried for about 15 minutes at about 50° C. and then humidified at about 50° C. for about 3 hours. The item is then dried for about 1 hour at about 35° C.

In the example of the previous paragraph, one entire test cycle takes approximately 24 hours. This test cycle may be repeated over several days until the desired results are achieved.

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
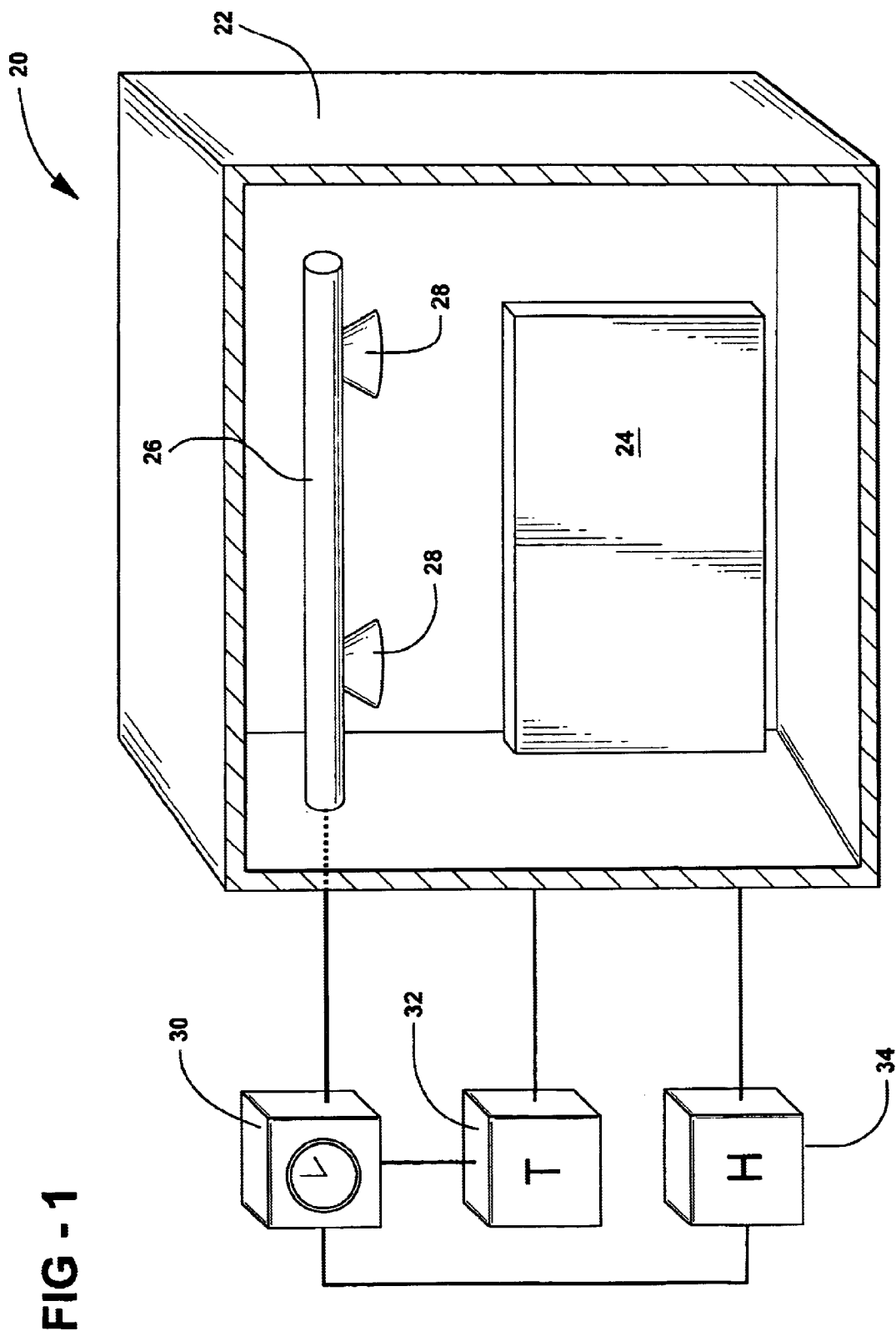
FIG. 1 schematically illustrates a testing arrangement that can be used to perform a method according to this invention.

A system 20 includes an enclosure 22 that is adapted to house a test item 24 for a simulating the effects of environmental factors on the item 24. A sprayer 26 includes a plurality of spray nozzles 28 for spraying a solution onto the item 24. In one example, the solution includes an electrolyte that is useful for simulating a marine atmosphere with some pollution content. In one example, the solution includes about 3.5% NaCl and about 0.35% $(NH4)_2SO_4$. This particular electrolyte is believed to accurately simulate a marine atmosphere with pollution. Other concentrations or other chemical combinations are within the scope of this invention. Those skilled in the art who have the benefit of this description will realize which chemical combinations will work best to simulate the particular environmental conditions in which they are interested.

A timer module 30, which may be part of a microprocessor, preferably controls the amount of time that the solution is applied to the item 24 using the sprayer assembly 26. The timer module 30 preferably also communicates with a temperature controller 32 and a humidity controller 34. The conditions within the enclosure 22 preferably are controlled so that a desired temperature and humidity level are achieved for chosen periods of time during a test cycle.

The various components of the system 20 are schematically illustrated. Given this description, those skilled in the art will be able to choose from among commercially available components to realize such a system.

A method according to this invention preferably subjects the item 24 to wet and dry conditions at various temperatures and for various lengths of time. The plot 40 in FIG. 2 graphically illustrates one example implementation of this invention. In this particular example, a marine environment is simulated. An entire test cycle in this example takes approximately 24 hours.

The times and temperatures during each phase or step are preferably controlled as accurately as possible using the timer module 30 and the controllers 32 and 34. Given the limitations of physical components, actual times and temperatures will vary. For example, it takes several minutes to achieve a temperature increase in the enclosure 22 so that a drying time at any increased temperature may not have the preferred temperature throughout the entire period. Similarly, adjustments in humidity levels may take some time to achieve a desired level for a given phase of the test cycle.

Within this description, time periods described are expected to vary as much as ten minutes in either direction (more or less). Therefore, a period described as about or approximately one hour should be understood to correspond to a period lasting anywhere from 50 minutes to 70 minutes. Wider variations are within the scope of this invention and a period described as about or approximately one hour may be understood to correspond to a period lasting anywhere from 35 minutes to 85 minutes. Target times are described for one example implementation of this invention. Variations of each time segment can be used in proportion to the target time.

Similarly, temperatures are expected to vary five degrees in either direction (higher or lower). Therefore, a temperature described as approximately or about 35° C. should be understood to correspond to a temperature within the range between 30° C. and 40° C. Further variation is within the scope of this invention and a temperature described as approximately or about 35° C. may be understood to correspond to a temperature within the range between 20° C. and 50° C.

Given the variety of test items and possible scenarios to simulate, variations are possible at each stage of a full test cycle to achieve an intended result. Given this description, those skilled in the art will realize how much to deviate from the specifics disclosed to meet their particular needs.

The example test cycle preferably takes about 24 hours and begins at 42 by spraying the solution onto the item 24 for a period lasting approximately 3 hours. The temperature within the enclosure 22 preferably is approximately 35° C. during this portion of the test cycle. The humidity level preferably is about 100% during this portion.

After the item 24 has been exposed to the solution, the item preferably is dried at a temperature of approximately 55° C. as shown at 44. The dry time of this portion of the test cycle preferably is approximately 1 hour and 45 minutes. The humidity level during drying times preferably is less than 50% relative humidity.

Next, at 46, the item is dried for approximately 15 minutes at a reduced temperature of approximately 50° C. Following that, at 48 the item 24 is exposed to humidity at the temperature of approximately 50° C. The item 24 preferably is humidified for approximately 3 hours. The preferred humidity level in one example is within the range from about 95% to 100% relative humidity.

After the 3 hours of humidification, the item 24 preferably is dried at a temperature of approximately 60° C. as shown at 50. The dry time of this portion of the test cycle preferably lasts approximately 1 hour and 45 minutes.

Figure 2:
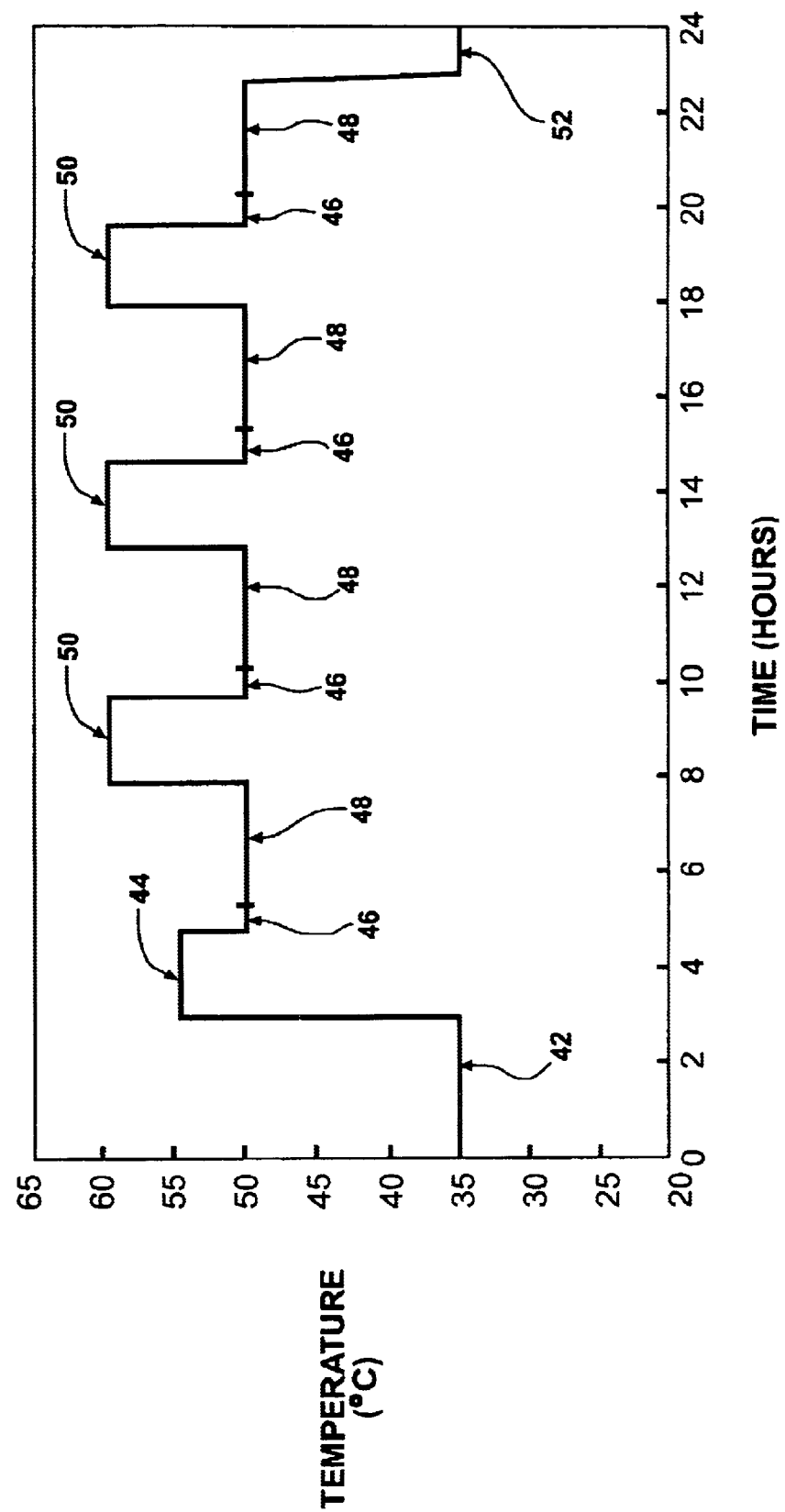
FIG. 2 graphically illustrates an example use of a method according to this invention.

The three steps illustrated at 46, 48 and 50 preferably are cyclically repeated three times as illustrated in FIG. 2. After the third drying time 50, the drying step 46 and humidification step 48 preferably are repeated one more time. The last portion 52 of the test cycle shown in FIG. 2 includes drying the item 24 at approximately 35° C. for about 1 hour.

Depending on the level of environmental exposure to be simulated, the test cycle illustrated in FIG. 2 may be repeated for many days. The total length of time of utilizing the inventive method will vary depending upon the test item composition and the desired exposure level simulation for a given situation. Those skilled in the art who have the benefit of this description will be able to determine how best to apply the inventive method to meet their particular need.

Figure 3:
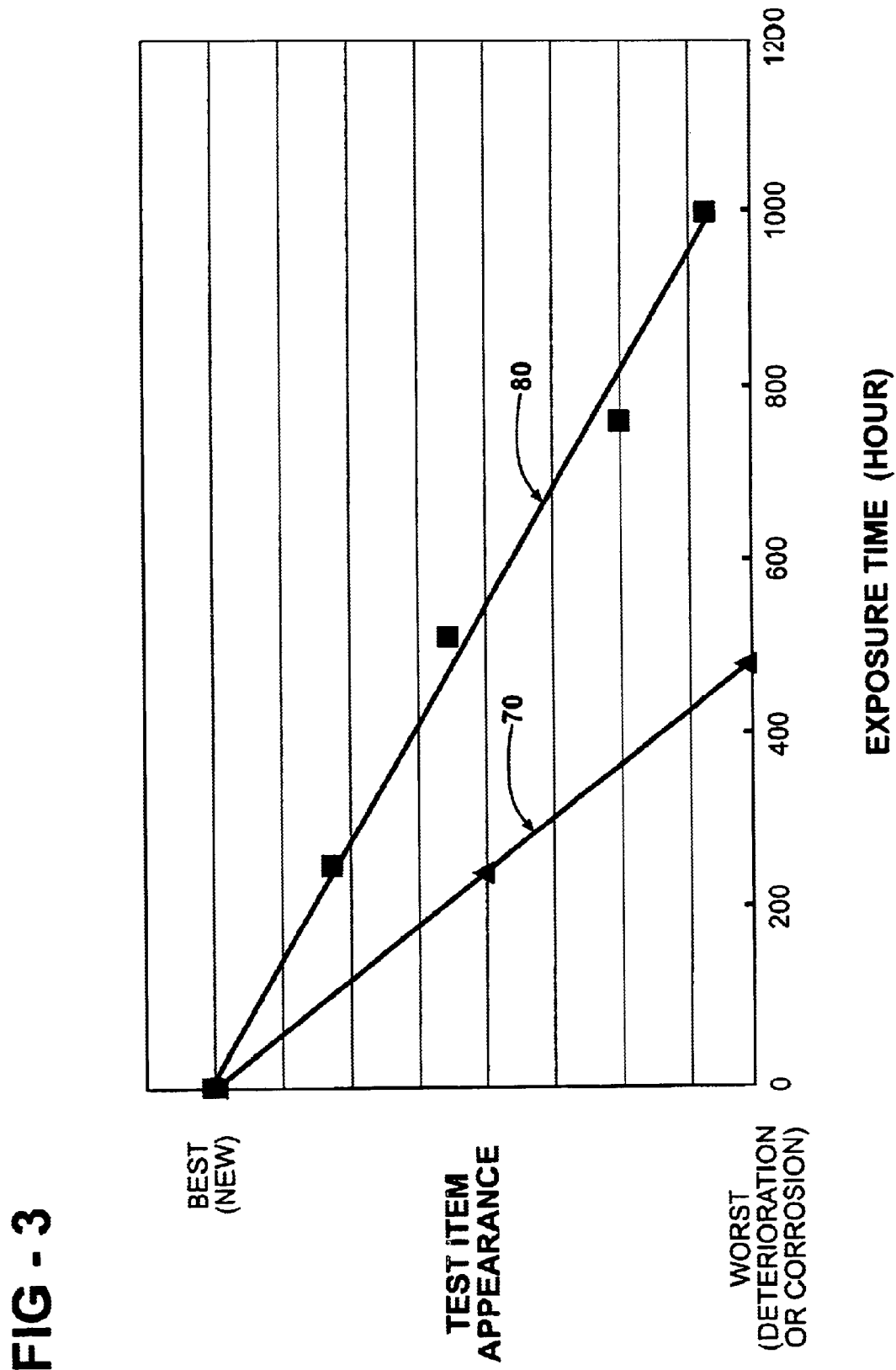
FIG. 3 graphically illustrates results of an example use of the inventive method compared to a conventional prohesion test method.

Utilizing the various exposure times and the different temperatures while the test item is exposed to wet or dry conditions provides a significantly accelerated environmental simulation test. Test results have shown that the inventive method reduces testing time between 4.5 and 9 times compared to the conventional Kure Beach 80 foot lot test, which includes actual exposure at a site at Kure Beach, N.C. The inventive method also has been demonstrated to have an acceleration factor that is 1.4 to 3 times faster than that available with the prohesion test. FIG. 3 graphically illustrates the acceleration rate of the above-described example at 70 compared to results on a test item using the conventional prohesion technique at 80. In the illustrated example, the same level of environmentally-induced corrosion was reached in about one-half the time using the inventive method. Moreover, the inventive method can be accurately correlated to actual field results.

The preceding description is exemplary rather than limiting in nature. Details regarding the currently preferred embodiment have been provided to explain the inventive method and to illustrate how the inventive method outperforms conventional techniques. Variations and modifications to the disclosed example may become apparent to those skilled in the art that do not necessarily depart from the essence of this invention. The scope of legal protection given to this invention can only be determined by studying the following claims.

We claim:

1. A method of simulating environmental exposure of an item, comprising the steps of:
   (A) wetting the item with a solution when the item is at a first temperature for a first length of time;
   (B) drying the item for a second length of time that is less than the first length at a second temperature that is higher than the first temperature;
   (C) drying the item for a third length of time that is less than the second length at a third temperature that is lower than the second temperature and higher than the first temperature;
   (D) humidifying the item when the item is at the third temperature for the first length of time;
   (E) drying the item for the second length of time at a fourth temperature that is higher than the second temperature;
   (F) repeating steps (C) and (D) after performing step (E); and
   (G) drying the item at the first temperature for a fourth length of time that is less than the second length of time and greater than the third length of time.

2. The method of claim 1, wherein the solution used in step (A) comprises about 3.5% NaCl and about 0.35% $(NH_4)_2SO_4$.

3. The method of claim 1, wherein the first length of time is about 3 hours, the second length of time is about 1 hour and 45 minutes, the third length of time is about 15 minutes and the fourth length of time is about 1 hour.

4. The method of claim 3, wherein the first temperature is about 35° C., the second temperature is about 55° C., the third temperature is about 50° C. and the fourth temperature is about 60° C.

5. The method of claim 1, wherein the first temperature is about 35° C., the second temperature is about 55° C., the third temperature is about 50° C. and the fourth temperature is about 60° C.

6. The method of claim 1, wherein steps (A) through (G) are performed sequentially within a 24 hour period.

7. The method of claim 1, wherein step (A) includes spraying the solution on the item.

8. The method of claim 1, including repeatedly performing the sequence of steps (A) through (G).

9. The method of claim 1, including placing the item in an enclosure where the temperature and humidity levels within the enclosure are controlled.

10. The method of claim 1, including repeating steps (C) through (E) sequentially twice before performing step (F).

11. A method of simulating environmental exposure of an item, comprising the steps of:

(A) wetting the item with a solution at about 35° C. for about 3 hours;

(B) drying the item for about 1 hour and 45 minutes at about 55° C.;

(C) drying the item for about 15 minutes at about 50° C.;

(D) humidifying the item at about 50° C. for about 3 hours;

(E) drying the item for about 1 hour and 45 minutes at about 60° C.;

(F) repeating steps (C) through (E) sequentially twice;

(G) repeating steps (C) and (D) each once after performing step (F); and (H) drying the item at about 35° C. for about 1 hour.

12. The method of claim 11, wherein the solution used in step (A) comprises about 3.5% NaCl+about 0.35% $(NH4)_2SO_4$.

13. The method of claim 11, wherein step (A) includes spraying the solution on the item.

14. The method of claim 11, including repeatedly performing the sequence of steps (A) through (H).

15. The method of claim 11, including placing the item in an enclosure where the temperature and humidity levels within the enclosure are controlled.

* * * * *